(12) United States Patent
Sawicz et al.

(10) Patent No.: US 12,102,567 B2
(45) Date of Patent: Oct. 1, 2024

(54) BEAM DETECTION WITH DUAL GAIN

(71) Applicant: Alcon Inc., Fribourg (CH)

(72) Inventors: Conrad Sawicz, Tustin, CA (US); Derek Y Chen, Irvine, CA (US)

(73) Assignee: Alcon Inc., Fribourg (CH)

( * ) Notice: Subject to any disclaimer, the term of this patent is extended or adjusted under 35 U.S.C. 154(b) by 269 days.

(21) Appl. No.: 17/491,986

(22) Filed: Oct. 1, 2021

(65) Prior Publication Data

US 2022/0110793 A1    Apr. 14, 2022

Related U.S. Application Data

(60) Provisional application No. 63/090,911, filed on Oct. 13, 2020.

(51) Int. Cl.
*A61F 9/008* (2006.01)
*H01S 3/10* (2006.01)

(52) U.S. Cl.
CPC ...... *A61F 9/00823* (2013.01); *H01S 3/10007* (2013.01)

(58) Field of Classification Search
CPC ............................... G01J 1/44; A61F 9/00823
See application file for complete search history.

(56) References Cited

U.S. PATENT DOCUMENTS

| | | | |
|---|---|---|---|
| 3,537,025 A | 10/1970 | Baum et al. | |
| 4,543,477 A * | 9/1985 | Doi | A61B 18/20 356/73.1 |
| 4,751,577 A | 6/1988 | Kawai | |
| 5,202,553 A | 4/1993 | Geller | |
| 5,329,560 A | 7/1994 | Rastegar et al. | |
| 5,336,882 A | 8/1994 | Fooks et al. | |
| 5,838,194 A | 11/1998 | Khoury | |
| 6,424,456 B1 | 7/2002 | Lee et al. | |
| 6,515,602 B2 | 2/2003 | Ahn et al. | |
| 6,710,658 B2 | 3/2004 | Griepentrog | |
| 7,961,770 B1 | 6/2011 | Zhu et al. | |
| 8,526,811 B2 | 9/2013 | Xie et al. | |
| 8,561,280 B2 | 10/2013 | Diao et al. | |
| 8,951,244 B2 | 2/2015 | Smith | |
| 9,054,479 B2 | 6/2015 | Karavitis | |
| 9,755,393 B2 | 9/2017 | Vogler et al. | |
| 10,778,335 B2 | 9/2020 | Prentice et al. | |
| 11,070,199 B2 | 7/2021 | Delong et al. | |
| 11,134,839 B2 | 10/2021 | Berke | |

(Continued)

FOREIGN PATENT DOCUMENTS

JP    2018022951 A    2/2018

*Primary Examiner* — Yingchuan Zhang
*Assistant Examiner* — Jessica L Mullins (57) ABSTRACT

Particular embodiments disclosed herein provide a surgical laser system comprising a laser source, a lens, a memory, and a processor in data communication with the memory and configured to execute instructions which cause the processor to control the laser source based on a detection signal received from a circuit. The circuit comprises a first amplifier, a second amplifier, and a switch coupled between the second amplifier and a reference potential node and whose state is based on an output of a first comparator. The circuit further comprises a second comparator coupled to the second amplifier and a logic gate coupled to the first comparator and the second comparator.

16 Claims, 4 Drawing Sheets

(56) References Cited

U.S. PATENT DOCUMENTS

2010/0253616 A1* 10/2010 Omi .................. G01J 1/0209
                                                                  250/214 R
2020/0107960 A1    4/2020  Bacher et al.

\* cited by examiner

BEAM DETECTION WITH DUAL GAIN

PRIORITY CLAIM

This application claims the benefit of priority of U.S. Provisional Patent Application Ser. No. 63/090,911 titled "BEAM DETECTION WITH DUAL GAIN," filed on Oct. 13, 2020, whose inventors are Conrad Sawicz and Derek Chen, which is hereby incorporated by reference in its entirety as though fully and completely set forth herein.

TECHNICAL FIELD

The present disclosure relates generally to a surgical laser system, and more specifically, to laser beam detection implemented with dual gain.

BACKGROUND

In a wide variety of medical procedures, laser light (e.g., illumination beam, laser treatment beam ("treatment beam"), laser aiming beam ("aiming beam"), etc.) is used to assist in surgery and/or treat patient anatomy. For example, in laser photocoagulation, a laser probe propagates a treatment beam to cauterize blood vessels at a laser burn spot across the retina. A treatment beam is typically transmitted from a surgical laser system through an optical fiber cable that proximally terminates in a port adapter, which connects to the surgical laser system, and distally terminates in the laser probe, which is manipulated by the surgeon. Note that, herein, a distal end of a component refers to the end that is closer to a patient's body while the proximal end of the component refers to the end that is facing away from the patient's body or in proximity to, for example, the surgical laser system.

In addition to cauterizing blood vessels at the laser burn spot, the treatment beam may also damage some of the rods and cones that are present in the retina that provide vision, thereby, affecting eyesight. Since vision is most acute at the central macula of the retina, the surgeon arranges the laser probe to generate a laser burn spot in the peripheral areas of the retina. During the procedure, the surgeon drives the probe with a non-burning aiming beam to illuminate the retinal area that is to be photocoagulated. Due to the availability of low-power red laser diodes, the aiming beam is generally a low-power red laser light. Once the surgeon has positioned the laser probe so as to illuminate a desired retinal spot with the aiming beam, the surgeon activates the treatment beam through a foot pedal or other means to photocoagulate the illuminated area (e.g., or an area encompassing the illuminated area) using the treatment beam. Having burned a retinal spot, the surgeon repositions the probe to illuminate a new spot with the aiming light, activates the treatment beam to photocoagulate the new spot, repositions the probe, and so on until a desired number of burned laser spots are distributed across the retina.

Certain types of laser probes coagulate or burn multiple spots at a time, which may result in a faster and more efficient photocoagulation. For example, a surgical laser system that is coupled to one of such laser probes through an optical fiber may be configured to split a single laser beam into multiple laser beams that exhibit a laser spot pattern. In such an example, the surgical laser system transmits the multiple laser beams to the optical cable, which may include an array of multiple optical fibers or a multi-core fiber that exhibit a corresponding fiber pattern.

For diabetic retinopathy, a pan-retinal photocoagulation (PRP) procedure may be conducted, and the number of required laser photocoagulations for PRP is typically large. For example, 1,000 to 1,500 spots are commonly burned. It may thus be readily appreciated that if the laser probe was a multi-spot probe enabling the burning of multiple spots at a time, the photocoagulation procedure would be faster (assuming the laser source power is sufficient). Accordingly, multi-spot/multi-fiber laser probes have been developed and described in U.S. Pat. Nos. 8,951,244 and 8,561,280 which are hereby incorporated by reference in their entirety as though fully and completely set forth herein. In addition to the aiming beam and the treatment beam, vitreoretinal procedures also benefit from illumination light or beam being directed into the eye and onto retinal tissue.

BRIEF SUMMARY

The present disclosure relates generally to a surgical laser system and more specifically to laser beam detection implemented with dual gain.

Certain embodiments of the present disclosure provide a surgical laser system comprising a laser source configured to propagate a laser beam, a memory comprising executable instructions, and a processor in data communication with the memory and configured to execute the instructions, which cause the processor to control the laser source based on a detection signal received from a circuit. The circuit comprises a first amplifier having an output coupled to an input of a first comparator and an input of a second amplifier, a switch coupled between the input of the second amplifier and a reference potential node, wherein a state of the switch is based on an output of the first comparator, a second comparator having an input coupled to an output of the second amplifier, wherein the first comparator has a first threshold voltage which is greater than a second threshold voltage of the second amplifier, and a logic gate having a first input coupled to an output of the first comparator and a second input coupled to an output of the second comparator. The surgical laser system further comprises a lens configured to focus the laser beam onto an interface plane of a proximal end of an optical fiber coupled to the surgical laser system though a port, wherein a distal end of the optical fiber is configured to project the laser beam onto a target surface.

Certain embodiments of the present disclosure provide a circuit comprising a first amplifier having an output coupled to an input of a first comparator and an input of a second amplifier, a switch coupled between the input of the second amplifier and a reference potential node, wherein a state of the switch is based on an output of the first comparator, a second comparator having an input coupled to an output of the second amplifier, wherein the first comparator has a first threshold voltage which is greater than a second threshold voltage of the second amplifier, and a logic gate having a first input coupled to an output of the first comparator and a second input coupled to an output of the second comparator.

Certain embodiments of the present disclosure provide a method of detecting a laser pulse by a circuit comprising receiving the laser pulse at an input of the circuit, generating an electrical signal based on the laser pulse, amplifying the electrical signal, performing a first comparison between the amplified electrical signal and a first threshold voltage, wherein a switch coupled to a reference potential node is closed when the amplified electrical signal is greater than the first threshold voltage. The method further comprises, based on the first comparison, performing a second comparison between the amplified electrical signal or the reference potential node to a second threshold voltage, wherein the first threshold voltage is greater than the second threshold voltage, amplifying an output generated by the second comparison, and generating, based on at least one of the output of the first comparison and the amplified output of the second comparison, a signal indicating detection of the laser pulse.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
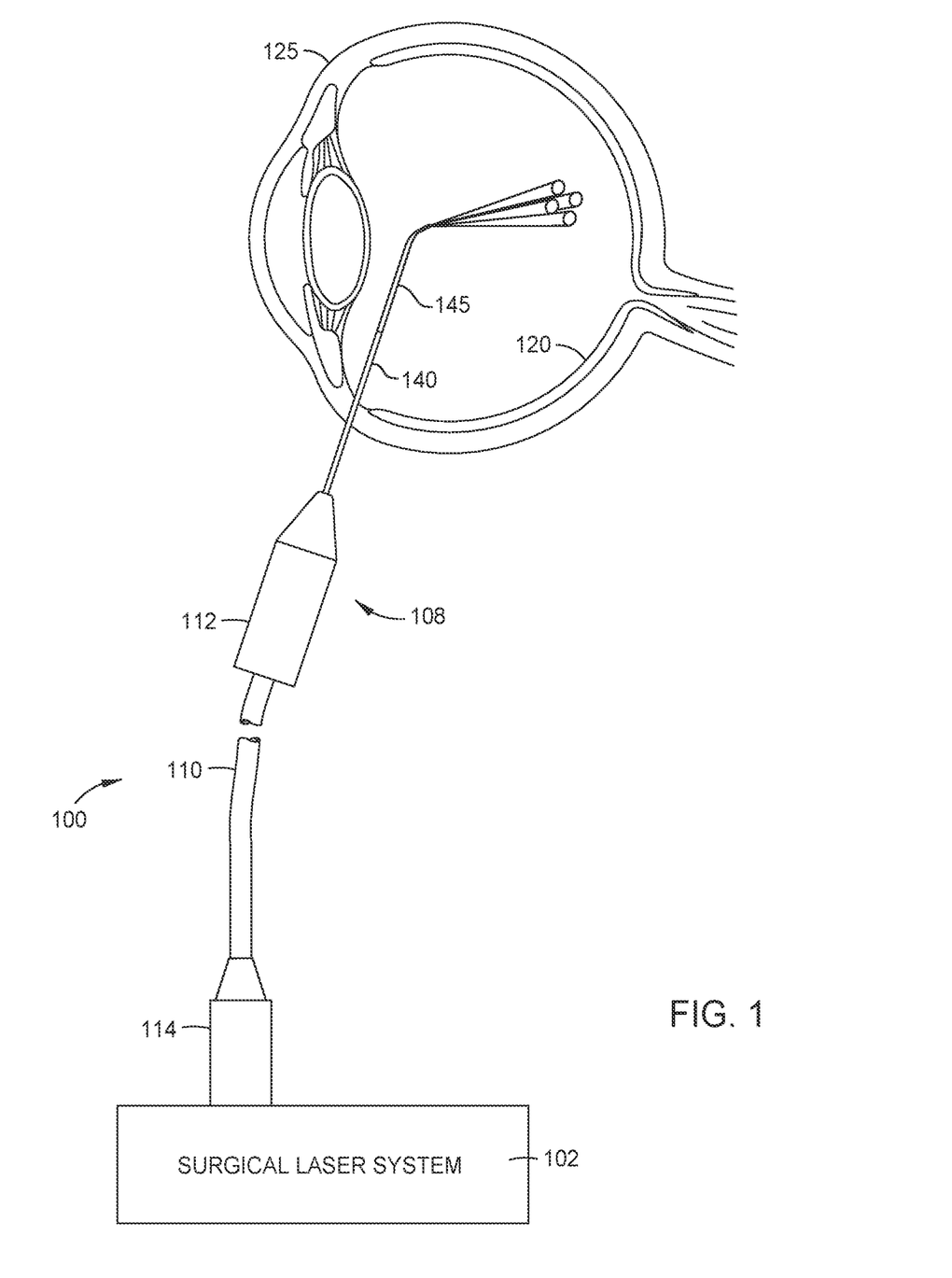
FIG. 1 illustrates an example system for laser beam detection implemented with dual gain beam detection, in accordance with certain aspects of the present disclosure.

Aspects of the present disclosure provide a surgical laser system with a laser beam detection circuit implemented with dual gain.
Example Surgical Laser System FIG. 1 illustrates an example system 100 having laser beam detection implemented with dual gain, according to certain embodiments. System 100 includes a surgical laser system 102 having one or more laser sources for generating laser beams used during ophthalmic procedures. For example, a first laser source within surgical laser system 102 may generate a treatment beam with a first wavelength (e.g., ~532 nanometers (nm)) while a second laser source may generate an aiming beam with a second wavelength (e.g., ~635 nm). A user, such as a surgeon, may first trigger the surgical laser system 102 (e.g., via a foot switch, voice commands, etc.) to emit the aiming beam onto a desired retinal spot. Once the surgeon has positioned the laser probe so as to illuminate the desired retinal spot with the aiming beam, the surgeon activates the treatment beam, such as through a foot pedal or other means, to treat patient anatomy (e.g., photocoagulate the desired retinal spot using the treatment beam).

As shown, surgical laser system 102 includes a connector or port adapter 114 that couples to an optical port of surgical laser system 102. FIG. 1 also shows a cable 110 having a distal end that couples to and extends through a probe 108 and a proximal end that couples to and extends through port adapter 114. In some cases, as further described herein, the cable 110 may include more than one cable. In the example of FIG. 1, port adapter 114 includes a ferrule with an opening that allows laser beams from surgical laser system 102 to be propagated into an interface plane (also referred to as a proximal entrance plane) of the proximal end of cable 110. In some examples, the surgical laser system 102 may include more than one port adapter. The interface plane of cable 110 comprises the exposed proximal ends of the one or more cores where laser beams may be directed to. In the example of FIG. 1, cable 110 is a multi-core optical fiber cable (MCF) with four cores. As such, the interface plane of the proximal end of cable 110 comprises the proximal ends of the four cores that are exposed through the opening of the ferrule.

Surgical laser system 102 may be configured to split a single laser beam that is generated by a laser source into multiple laser beams that exhibit a laser spot pattern. For example, surgical laser system 102 may split an aiming beam into four aiming beams and then deliver the four aiming beams to the interface plane of cable 110 through the opening of the ferrule of port adapter 114. Surgical laser system 102 may further be configured to split the treatment beam into four treatment beams and deliver the four treatment beams to the interface plane of cable 110 through the opening of the ferrule. In such an example, each of the cores of cable 110 would then be transmitting a multi-wavelength or combined beam, which may refer to a treatment beam combined with an aiming beam. Though certain aspects are described with respect to the cores of the cable transmitting a combined beam, it should be noted that the cores of the cable 110 can also individually transmit either the treatment beam or the aiming beam, depending on which beam(s) are activated and incident on the cable 110.

In some examples, surgical laser system 102 may also propagate an illumination beam into an interface plane of cable 110 (e.g., which may also include a proximal end of a cladding that holds the cores within cable 110) in order to illuminate the inside of the eye, especially areas of the retina 120 that are to be photocoagulated. In certain aspects, an illumination beam may be propagated by a white light-emitting diode (LED).

Cable 110 delivers the combined beams to probe 108, which propagates a multi-spot pattern (e.g., four spots) of combined beams to the retina 120 of a patient's eye 125. Probe 108 includes a probe body 112 and a probe tip 140 that house and protect the distal end of cable 110. A distal end portion 145 of the probe tip 140 may also contain a lens that focuses the combined beams on the retina 120.

Figure 2:
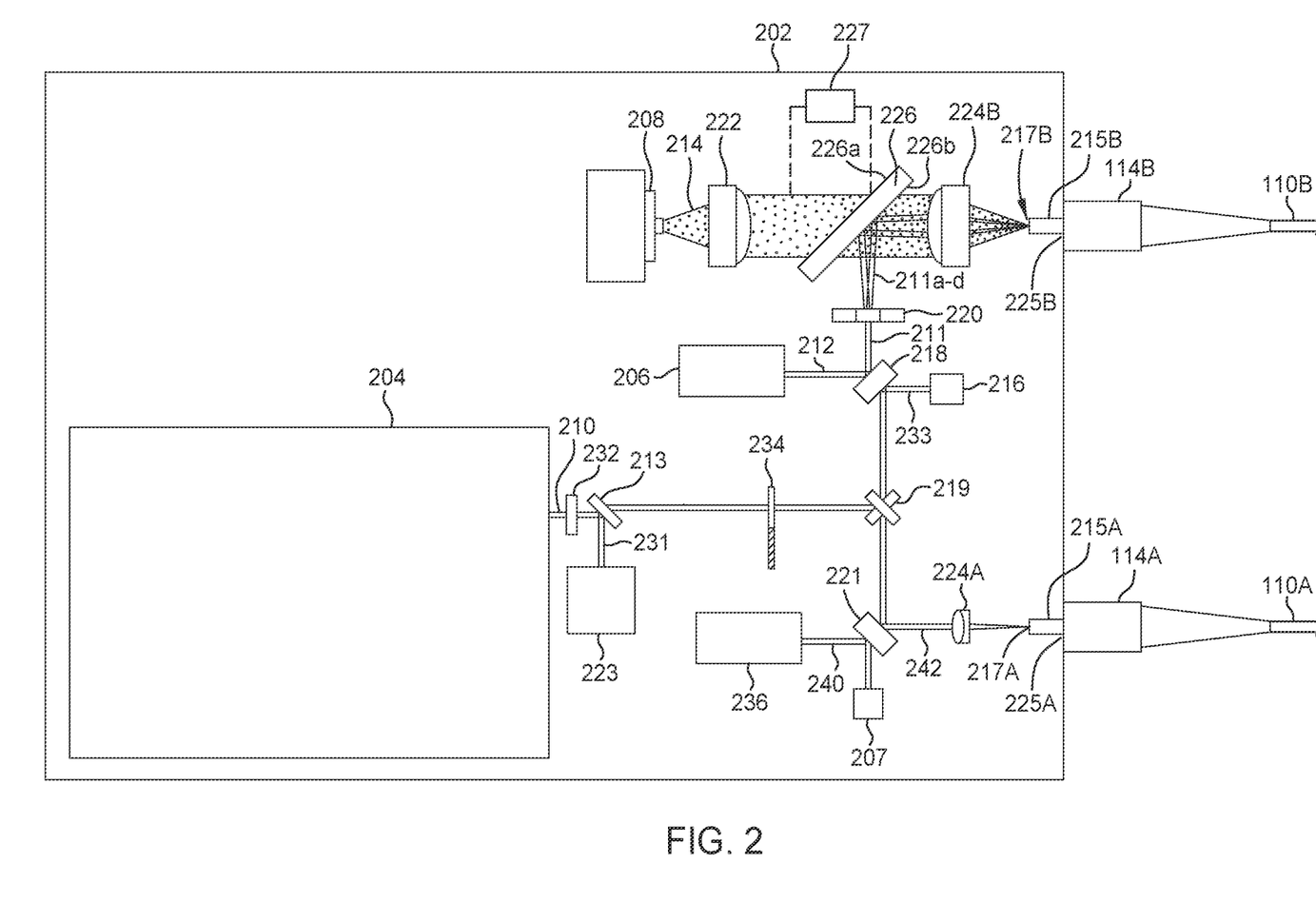
FIG. 2 illustrates an example of a surgical laser system, and the components therein, implemented with dual gain beam detection, in accordance with certain aspects of the present disclosure.

Various systems can be implemented with dual gain laser detection circuitry. FIG. 2 illustrates one example of a surgical laser system 202, and the components therein, that may be implemented with beam detection circuitry having dual gain. Surgical laser system 202 comprises a laser source 204, which propagates a treatment beam 210, laser sources 206, 236, which propagate aiming beams 212, 240, respectively, a light source 208, which propagates an illumination beam 214, a port selector 219, and beam detection circuitry 207, 216.

At the outset of the surgery, a surgeon may activate light source 208 in order to illuminate the inside of the eye's globe and make it easier to view the retina. As shown, once emitted by light source 208, illumination beam 214 (stippled segment) is received by collimating lens 222, which is configured to produce a beam with parallel rays of light. In certain embodiments, collimating lens 222 may be a multi-element achromat comprising two singlet lenses and one doublet lens. Therefore, as shown, illumination beam 214 emerges with parallel rays of light from the other side of collimating lens 222 and passes through beam splitter 226 to reach a condensing lens 224B. In certain embodiments, condensing lens 224B may be a multi-element achromat comprising two singlet lenses and one doublet lens. In such embodiments, condensing lens 224B has the same design as collimating lens 222, except that the assembly is revered (e.g., rotated by 180 degrees), thereby creating a one-to-one magnification imaging system. Beam splitter 226 may have different coatings on its two sides, 226a and 226b. For example, side 226a is coated such that it allows light propagated thereon to pass through beam splitter 226. As such, illumination beam 214, which is propagated onto side 226a passes beam splitter 226. On the other hand, side 226b is coated to reflect light or laser beams such as treatment beam 210 and aiming beam 212, as further described below. Although, note that a trivial portion of illumination beam 214 is reflected by side 226a onto sensor 227, which is configured to sense illumination beam 214.

Condensing lens 224B then converges illumination beam 214 into an interface plane of a proximal end of a cable, such as cable 110B, which is coupled to port 225B of surgical laser system 202 through port adapters 114B. As described in relation to FIG. 1, the cable 110B may have four cores. As such, condensing lens 224B focuses illumination beam 214 into an interface plane of cable 110B such that illumination beam 214 is propagated, along an entire length of each of the four cores of cable 110B, to the distal end of a surgical probe (e.g., probe 108 of FIG. 1) that is coupled to cable 110B. As described above, the interface plane of each of cables 110A, 110B comprises the proximal ends of the four cores of cable 110 that are exposed through openings 217A, 217B of port adapters 114A, 114B, respectively, via ferrules 215A, 215B.

Once the surgeon is able to view inside the eye's globe, the surgeon may project from the distal end of the probe one or more desired aiming beam spots onto the retina. More specifically, after activation by the surgeon, laser source 206 emits aiming beam 212 onto beam splitter 218, which reflects aiming beam 212 onto diffraction optical element (DOE) 220. Similarly, the laser source 236 emits aiming beam 240 onto beam splitter 221, which passes a portion of aiming beam 240 toward the condensing lens 224A, which focuses the aiming beam 240 into an interface plane of cable 110A such that aiming beam 240 is propagated, along an entire length of each core of cable 110A, to the distal end of a surgical probe (e.g., probe 108 of FIG. 1) that is coupled to cable 110A. A diffraction segment may also be referred to as a "segment" herein. In the example of FIG. 2, DOE 220 is positioned such that aiming beam 212 is aligned with the middle segment of DOE 220, which diffracts aiming beam 212 into aiming beams (e.g., four aiming beams). However, a surgeon may change the position of DOE 220 in order to diffract a beam into a different number of beams (e.g., 2 or 1). For example, using voice command or some other feature of surgical laser system 202, a surgeon may position DOE 220 to align aiming beam 212 with a different segment of DOE 220, which may diffract aiming beam 212 into two or one or other numbers of beams.

Once diffracted, the resulting aiming beams are reflected by beam splitter 226 onto condensing lens 224B. Condensing lens 224B then focuses the four aiming beams onto the interface plane of a proximal end of cable 110B such that each of the aiming beams is propagated, along an entire length of a corresponding core of cable 110B, to the distal end of a surgical probe (e.g., probe 108 of FIG. 1). This allows the surgeon to project from the distal end of the probe four desired aiming beam spots onto the retina.

As described above, once the surgeon has positioned and activated the laser probe so as to project aiming beam spots onto the retina, the surgeon activates laser source 204, such as through a foot pedal or other means, to treat patient anatomy (e.g., photocoagulate the desired retinal spot using the treatment beam). When activated, laser source 204 emits polarized treatment beam 210, whose polarization axis may be changed by a polarization rotator 232. For example, in some embodiments, polarization rotator 232 filters treatment beam 210 to produce a vertically-polarized treatment beam which is s-polarized relative to the plane of incidence of beam splitter 226.

A polarized treatment beam 210 may be advantageous because beam splitter 226 may have coatings that are sensitive to polarization such that, for example, an s-polarized beam may reflect off of beam splitter 226 with less broadening of the wavelength. As described above, beam splitter 226 is coated such that it allows illumination beam 214 to pass through while reflecting treatment beam 210 and aiming beam 212. Therefore, to provide the surgeon with a high quality and throughput of illumination beam 214A, it is advantageous to polarize treatment beam 210, which allows beam splitter 226 to isolate and reflect treatment beam 210 with a narrower band of wavelength.

The surgical laser system may also include a shutter 234 arranged between the laser source 204 and the port selector 219. The shutter 234, may be configured to alternatively block or permit the treatment laser beam from reaching the port selector 219. A surgeon or surgical staff member can control the shutter 234 (e.g., via a foot switch, voice commands, etc.) to emit the laser aiming beam and fire the treatment laser beam (i.e., open the shutter 234) to treat patient anatomy (e.g., photocoagulation). In each case, the beam splitter 221 and the beam splitter 218 may direct the laser beams towards the first port adapter 114A and the second port adapter 114B, respectively.

Once polarized, treatment beam 210 reaches beam splitter 213, which is configured to allow a substantial portion of treatment beam 210 to pass through, while reflecting a trivial portion 231 onto sensor 223. Sensor 223 is a light sensor configured to detect whether laser source 204 is active or not. After passing through beam splitter 213 and provided that the shutter 234 is in an open position to permit the treatment beam 210, treatment beam 210 is received at port selector 219, which is configured to reflect treatment beam 210 onto beam splitter 218 or beam splitter 221. Beam splitter 218 is configured to reflect a trivial portion 233 of treatment beam 210 onto beam detection circuitry 216 while allowing a substantial portion of treatment beam 210 to pass through. As described further herein, beam detection circuitry 216 is a light sensing circuitry implemented with dual gain. Beam splitter 221 is configured to reflect a portion of treatment beam 210 onto the condensing lens 224A while allowing another portion of treatment beam 210 to pass through to beam detection circuitry 207, which may be similar to beam detection circuitry 216.

As shown, linearly polarized treatment beam 210 passes through beam splitter 221 at an angle with respect to beam splitter 221 that is equal to the angle with which aiming beam 240 is passed by beam splitter 221. Therefore, once laser source 204 is active, transmitted treatment beam 210 and reflected aiming beam 240 are combined (e.g., such that they overlay each other), creating combined beam 242, before reaching condensing lens 224A. Condensing lens 224A focuses combined beam 242 onto an interface plane of the proximal end of cable 110A such that the combined beam 242 is propagated, along an entire length of the core of cable 110A, to the distal end of a surgical probe (e.g., probe 108 of FIG. 1).

As shown, linearly polarized treatment beam 210 passes through beam splitter 218 at an angle with respect to beam splitter 218 that is equal to the angle with which aiming beam 212 is reflected by beam splitter 218. Therefore, once laser source 204 is active, transmitted treatment beam 210 and reflected aiming beam 212 are combined (e.g., such that they overlay each other), creating combined beam 211, before reaching DOE 220. DOE 220 then diffracts combined beam 211 into combined beams 211a-211d. Each one of combined beams 211a-211d refers to a diffracted treatment beam and a diffracted aiming beam that overlay each other.

Combined beams 211a-211d are then received at beam splitter 226, which reflects combined beams 211a-211d onto condensing lens 224B. Condensing lens 224B focuses combined beams 211a-211d onto an interface plane of the proximal end of cable 110B such that each of the combined beams 211a-211d is propagated, along an entire length of a corresponding core of cable 110B, to the distal end of a surgical probe (e.g., probe 108 of FIG. 1). More specifically, in the example of FIG. 2, cable 110B is an MCF with four cores, such as cores A, B, C, and D. In such an example, condensing lens 224B focuses combined beams 211a-211d onto an interface plane of a proximal end of cable 110B such that, for example, combined beam 211a is propagated onto core A, combined beam 211b is propagated onto core B, combined beam 211c is propagated onto core C, and combined beam 211d is propagated onto core D.

Example Beam Detection with Dual Gain

Aspects of the present disclosure provide a surgical laser system with a laser beam detection circuit implemented with dual gain. In particular, certain aspects provide techniques for measuring a pulse duration, such as of short (e.g., 50 μs (microseconds)) laser pulses that may have a wide dynamic range (e.g., 1 mW (milliwatt) to 3.3 W (Watts)).

Currently, measuring short laser pulses may be accomplished with circuits that generally ignore pulse amplitude by merely limiting the circuit gain. Gain-limiting circuits usually have a recovery time (e.g., 10 μs or longer) that takes up a substantial proportion of the laser pulse duration (e.g., 50 μs). As a result, such recovery time may cause errors in measuring the actual laser pulse duration. Photodiode beam detectors may be implemented in such circuits, often for two separate purposes. The first purpose is to detect the laser pulse when the laser pulse is on to verify the laser beam is being steered to a correct output port. The duration of the detected signal may be measured to verify the pulse duration. The second purpose is to detect unwanted output, which can potentially occur when pulses are generated using micropulsing. For example, laser energy can be directed to an incorrect port or the laser appears to be on when the laser is meant to be off. Improper or inaccurate detection of the laser beam can be hazardous to patients during medical procedures involving laser beams.

The dynamic range of a laser beam may be large. That is, the maximum output can be as high as 3.3 W, and as low as 1 mW. Accommodating the relatively large dynamic range of the laser beam may be further complicated by the uncertainty in beam splitters used to sample the laser beam itself. For example, the manufacturing variation can be as high as 100% in the beam splitters. It may be desirable for the circuit used for detecting an output of a photodiode that receives the laser pulse to be able to handle the large dynamic range, while still capable of measuring the pulse duration accurately.

Conventional gain-limiting circuits usually affect the ability of the circuit to measure the pulse duration accurately. There are several ways to amplify a photodiode signal; however, high-speed response is usually best accomplished using a trans-impedance (TIM) amplifier. As long as the amplifier stays inside its operating limits, the pulse fidelity is generally high. However, when the output signal is too large, the amplifier may saturate, causing the recovery time to be unpredictable or very long. Zener diodes can be used to limit the volt gain to that of the Zener diode's breakdown voltage, but the Zener diode saturation recovery time can be equal to or greater than 10 μs. Thus, a circuit that can handle the dynamic range of a laser beam and does not saturate is desired for proper and accurate pulse measurement.

Accordingly, certain aspects of the present disclosure provide techniques for a beam detection circuit implemented with dual gain. In particular, certain aspects relate to using two amplifiers with different gains in series in a beam detection circuit. The first amplifier's gain may be set such that the largest laser pulse will be inside the operating limits of the first amplifier. The second amplifier may have a gain to further amplify a signal such that low amplitude pulses can be measured by the circuit. An output of the first amplifier may control a switch that may be configured to block the signal to the second amplifier when a large pulse (e.g., greater than a threshold voltage) is detected. In other words, the output from the first amplifier may be shunted (e.g., shorted) to a reference potential node (e.g., ground). By blocking the signal to the second amplifier, the second amplifier may be prevented from exceeding its operating limits when a particularly large signal is being passed through the circuit. In certain aspects, the output of the first amplifier and/or the second amplifier may be used to measure the pulse duration such that switching amplifiers does not affect the measurement. In other words, implementing the beam detection circuit with two amplifiers in the fashion described above allows for more accurate detection of laser beams.

Figure 3:
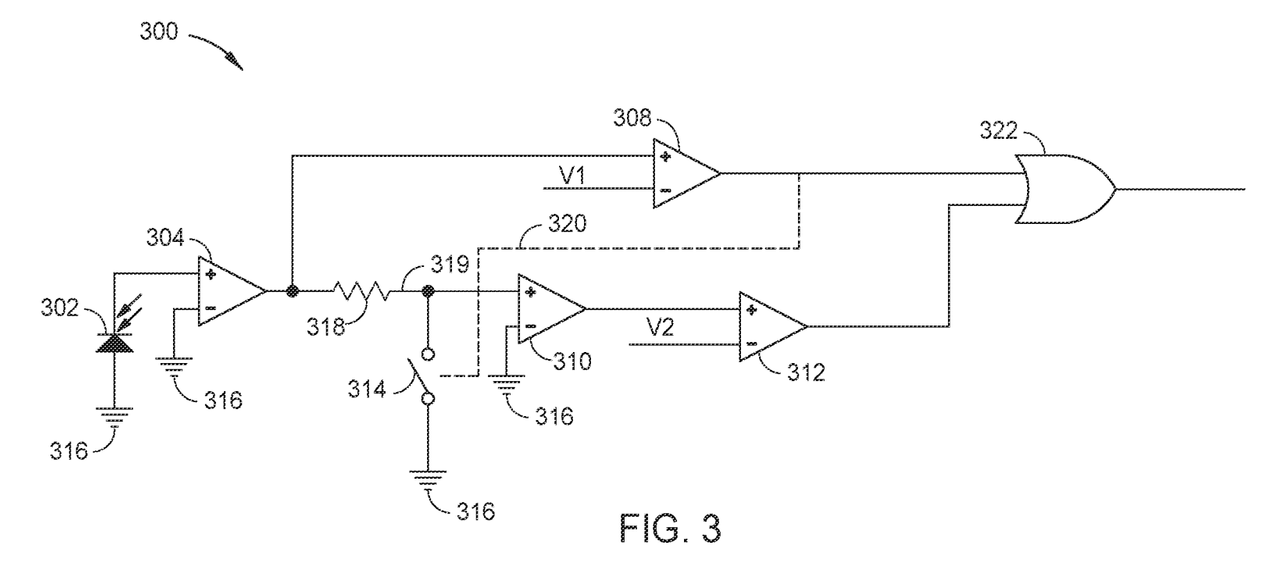
FIG. 3 illustrates an example circuit implemented with dual gain beam detection, in accordance with certain aspects of the present disclosure.

FIG. 3 illustrates an example circuit 300 implemented with dual gain beam detection.

As shown, the circuit 300 may include a photodiode 302, amplifiers 304, 310, comparators 308, 312, a switch 314, a resistor 318, and a logic gate 322.

As illustrated, the photodiode 302 may be coupled between an input of the amplifier 304 and a reference potential node 316 (e.g., electrical ground). In some embodiments, the reference potential node 316 may instead be a voltage or current source. Another input of the amplifier 304 may be coupled to the reference potential node 316. In certain aspects, the amplifier 304 may amplify a photodiode signal as much as possible without exceeding the operational limits of the amplifier 304. An output of the amplifier 304 may be coupled to an input of the amplifier 310, which may have another input coupled to the reference potential node 316. In certain aspects, the gain of the amplifier 310 may be greater than the gain of the amplifier 304. As shown, the resistor 318 may be coupled between the amplifiers 304, 310. Furthermore, the switch 314 may be coupled between a node 319 (between the resistor 318 and the amplifier 310) and the reference potential node 316.

The output of the amplifier 304 may be coupled to an input of the comparator 308, and that input may be compared to a voltage $V_1$. As shown, an output of the amplifier 310 may be coupled to an input of the comparator 312, and that input may be compared to the voltage $V_2$. In certain aspects, $V_1$ may be greater than $V_2$, and $V_2$ may be selected to be sufficiently large (e.g., a value that is exceeded when the laser pulse exceeds 1 mW) such that noise does not cause a false triggering. $V_1$ may be chosen to be greater than $V_2$ since the comparator 312 may be configured for detecting low power beams (e.g., as low as 1 mW laser beams) and may saturate due to higher power beams, while the comparator 308 may be configured for detecting higher power beams without saturation (e.g., up to 3.3 W laser beams). If the input to the comparator 308 exceeds the voltage $V_1$, then the comparator 308 may output a logic high voltage signal (e.g., 3.3V or 5V) to the logic gate 322, as well as to the switch 314, as indicated by the dashed line 320. If the input to the comparator 312 exceeds the voltage $V_2$, then the comparator 312 may output a logic high voltage signal (e.g., 3.3V or 5V) to the logic gate 322. When the output of the comparator 308 is logic high, for example, the switch 314 may close and couple (e.g., short) the input of the amplifier 310 to the reference potential node 316. In certain aspects, the logic gate 322 may be an OR gate, or any other suitable logic gate.

In certain aspects, it may be advantageous for the photodiode signal to be amplified such that an approximately 1 mW signal exceeds the threshold. However, a signal whose power is significantly higher than 1 mW (e.g., a high level signal), when amplified by the amplifier 304, would cause the amplifier 310 to exceed its operating limits. Thus, the voltage V1 of the comparator 308 may be selected such that the voltage $V_1$ is less than the saturation voltage of the amplifier 310. When a high level signal is then passed through the circuit 300, such a signal may cause a logical high output from the comparator, and subsequently close the switch 314, before the amplifier 310 reaches the saturation voltage. A low-level laser pulse (e.g., a low power laser pulse) may be applied to the photodiode and be amplified by both of amplifiers 304, 310. This technique may prevent the amplifier 310 from significant overload so the amplifier 310 can, for example, return to a zero output fast enough to not affect the pulse measurement. Since the amplifier 304 has a finite rise time, the comparator 312 may output a logic high signal before the signal has sufficient amplitude to trigger the comparator 308, and, consequently, cause the switch 314 to close. In the case of one or more of the comparators 308, 312 outputting a logic high signal, the logic gate 322 may output a logic high signal. The output of the logic gate 322 may cause a timer to start, for example, to measure the duration of the laser pulse. Thus, the start of a laser pulse can be measured with similar accuracy for both large and small amplitude pulses (e.g., high or low level signals). In some implementations, laser pulses may be timed and/or controlled independently of the circuit 300. For example, this may be done by a shutter (e.g., the shutter 234 of FIG. 2) or a power supply. In this case, the circuit 300 may be used as a double check for the laser pulse timing. Further, in some examples of independent pulse timing/controlling, the photodiode timing may be measured by two independent circuits such that the clocks used to create/measure the pulse are independent.

Figure 4:
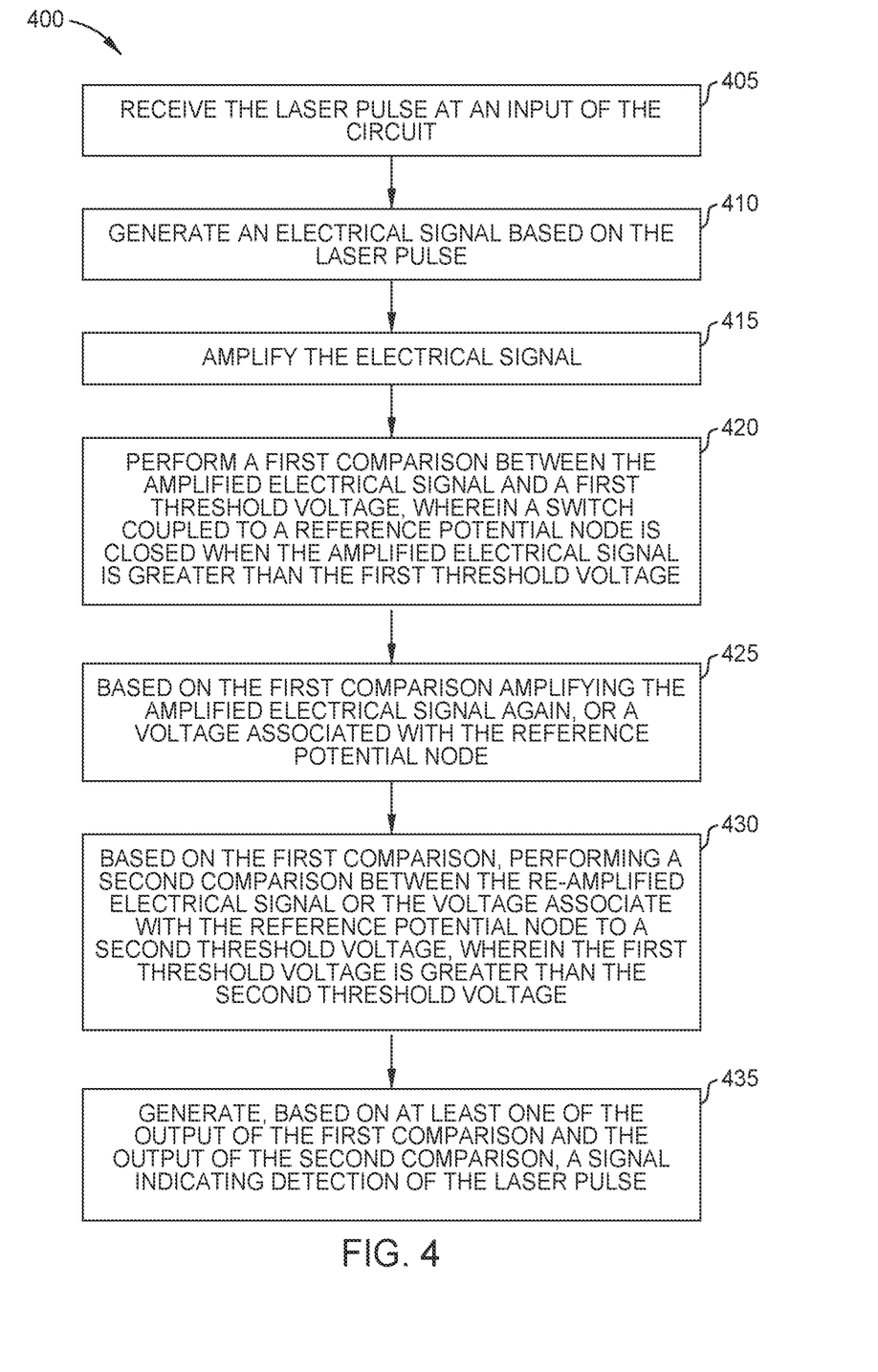
FIG. 4 is a flow diagram illustrating example operations of detecting a laser pulse by a circuit, in accordance with certain aspects of the present disclosure.

FIG. 4 is a flow diagram illustrating example operations 400 of detecting a laser pulse by a circuit. Operations 400 may be understood and implemented within the scope of the circuit 300 of FIG. 3.

Operations 400 begin, at block 405, by receiving the laser pulse at an input of the circuit. At 410, the circuit generates (e.g., via the photodiode 302) an electrical signal based on the laser pulse. At 415, the circuit amplifies (e.g., via the amplifier 304) the electrical signal.

At 420, the circuit performs a first comparison (e.g., via the comparator 308) between the amplified electrical signal and a first threshold voltage (e.g., the voltage $V_1$), wherein a switch (e.g., the switch 314) coupled to a reference potential node (e.g., the reference potential node 316) is closed when the amplified electrical signal is greater than the first threshold voltage.

At 425, based on the first comparison, the circuit amplifies (e.g., via the amplifier 310) the amplified electrical signal again or a voltage associated with the reference potential node. In certain aspects, the amplified electrical signal may be amplified again when the voltage of the amplified electrical signal is less than the first threshold voltage. When the voltage of the amplified electrical signal is greater than the first threshold voltage, the amplified electrical signal is coupled to the reference potential, thereby effectively shunting/shorting the amplified electrical signal. Thus, the amplified electrical signal is not passed to the second amplifier. Rather, as a consequence, the voltage associated with the reference potential node (e.g., ground) may be input into the second amplifier.

At 430, based on the first comparison, the circuit performs a second comparison (e.g., via the comparator 312) between the re-amplified electrical signal or the voltage associated with the reference potential node to a second threshold voltage (e.g., the voltage $V_2$), wherein the first threshold voltage is greater than the second threshold voltage.

At 435, the circuit generates (e.g., via the logic gate 322), based on at least one of the output of the first comparison and the output of the second comparison, a signal indicating detection of the laser pulse.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Example Embodiments

Embodiment 1: a surgical laser system, including a laser source configured to propagate a laser beam, a memory comprising executable instructions, a processor in data communication with the memory and configured to execute the instructions, which cause the processor to control the laser source based on a detection signal received from a circuit. The circuit including a first amplifier having an output coupled to an input of a first comparator and an input of a second amplifier, a switch coupled between the input of the second amplifier and a reference potential node, wherein a state of the switch is based on an output of the first comparator, a second comparator having an input coupled to an output of the second amplifier, wherein the first comparator has a first threshold voltage which is greater than a second threshold voltage of the second amplifier, and a logic gate having a first input coupled to an output of the first comparator and a second input coupled to an output of the second comparator. The surgical laser system further includes a lens configured to focus the laser beam onto an interface plane of a proximal end of an optical fiber coupled to the surgical laser system though a port, wherein a distal end of the optical fiber is configured to project the laser beam onto a target surface.

Embodiment 2: the surgical laser system of embodiment 1, wherein the circuit further includes a photodiode coupled between an input of the first amplifier and a reference potential node, the photodiode being configured to receive the laser beam.

Embodiment 3: the surgical laser system of embodiment 1 or 2, wherein the processor is configured to start a timer when the processor receives the detection signal from the circuit, and the processor is configured to cease propagation of the laser beam when the timer reaches a timing threshold value.

Embodiment 4: the surgical laser system of any of embodiments 1-3, wherein the processor is configured to cease propagation of the laser beam, except upon determining, based on the detection signal that the laser beam is directed to the port, the laser beam is propagated when the surgical laser system is directed to propagate the laser beam and not when the surgical system is not directed to propagate the laser beam, and the laser beam is propagated within a threshold duration of time.

Embodiment 5: the surgical laser system of any of embodiments 1-4, further including a photodiode coupled between an input of the first amplifier and the reference potential node.

Embodiment 6: the surgical laser system of any of embodiments 1-5, wherein the first amplifier has a first gain less than a second gain of the second amplifier.

Embodiment 7: the surgical laser system of any of embodiments 1-6, wherein a saturation voltage level of the second amplifier is greater than the first threshold voltage of the first comparator.

Embodiment 8: the surgical laser system of any of embodiments 1-7, wherein the second threshold voltage of the second comparator is at least 1 mW.

Embodiment 9: the surgical laser system of any of embodiments 1-8, wherein the switch is configured to short the input of the second amplifier to the reference potential node if a voltage at the input of the first comparator exceeds the first threshold voltage of the first comparator.

Embodiment 10: the surgical laser system of any of embodiments 1-9, wherein the switch is one of an analog switch or a metal oxide semiconductor field effect transistor (MOSFET).

Embodiment 11: the surgical laser system of any of embodiments 1-10, wherein the first amplifier is a transimpedance amplifier.

Embodiment 12: the surgical laser system of any of embodiments 1-11, wherein the logic gate is an OR gate.

Embodiment 13: the surgical laser system of any of embodiments 1-12, further including a resistor coupled between the output of the first amplifier and the input of the second amplifier.

Embodiment 14: a method of detecting a laser pulse by a circuit, comprising receiving the laser pulse at an input of the circuit, generating an electrical signal based on the laser pulse, amplifying the electrical signal, performing a first comparison between the amplified electrical signal and a first threshold voltage, wherein a switch coupled to a reference potential node is closed when the amplified electrical signal is greater than the first threshold voltage, based on the first comparison, amplifying the amplified electrical signal again, or shunting the amplified electrical signal to the reference potential node, performing a second comparison between the re-amplified electrical signal to a second threshold voltage when the amplified electrical signal is re-amplified, wherein the first threshold voltage is greater than the second threshold voltage, and generating, based on at least one of the output of the first comparison and the output of the second comparison, a signal indicating detection of the laser pulse.

Embodiment 15: a circuit, including a first amplifier having an output coupled to an input of a first comparator and an input of a second amplifier, a switch coupled between the input of the second amplifier and a reference potential node, wherein a state of the switch is based on an output of the first comparator, a second comparator having an input coupled to an output of the second amplifier, wherein the first comparator has a first threshold voltage which is greater than a second threshold voltage of the second amplifier, and a logic gate having a first input coupled to an output of the first comparator and a second input coupled to an output of the second comparator.

Embodiment 16: the circuit of embodiment 15, further including a photodiode coupled between an input of the first amplifier and the reference potential node.

Embodiment 17: the circuit of embodiment 15 or 16, wherein the first amplifier has a first gain less than a second gain of the second amplifier.

Embodiment 18: the circuit of any of embodiments 15-17, wherein a saturation voltage level of the second amplifier is greater than the first threshold voltage of the first comparator.

Embodiment 19: the circuit of any of embodiments 15-18, wherein the second threshold voltage of the second comparator is at least 1 mW.

Embodiment 20: the circuit of any of embodiments 15-19, wherein the switch is configured to short the input of the second amplifier to the reference potential node if a voltage at the input of the first comparator exceeds the first threshold voltage of the first comparator.

Embodiment 21: the circuit of any of embodiments 15-20, wherein the switch is one of an analog switch or a metal oxide semiconductor field effect transistor (MOSFET).

Embodiment 22: the circuit of any of embodiments 15-21, wherein the first amplifier is a transimpedance amplifier.

Embodiment 23: the circuit of any of embodiments 15-22, wherein the logic gate is an OR gate.

Embodiment 24: the circuit of any of embodiments 15-23, further including a resistor coupled between the output of the first amplifier and the input of the second amplifier.

What is claimed is:

1. A surgical laser system, comprising:
a laser source configured to propagate a laser beam;
a memory comprising executable instructions;
a processor in data communication with the memory and configured to execute the instructions, which cause the processor to control the laser source based on a detection signal received from a circuit, the circuit comprising:
a first amplifier having an output coupled to an input of a first comparator and an input of a second amplifier;
a switch coupled between the input of the second amplifier and a reference potential node, wherein a state of the switch is controlled based on an output of the first comparator;
a second comparator having an input coupled to an output of the second amplifier, wherein the first comparator has a first threshold voltage which is greater than a second threshold voltage of the second comparator; and
a logic gate having a first input coupled to an output of the first comparator and a second input coupled to an output of the second comparator, wherein an output of the logic gate is the detection signal; and a lens configured to focus the laser beam onto an interface plane of a proximal end of an optical fiber coupled to the surgical laser system through a port, wherein a distal end of the optical fiber is configured to project the laser beam onto a target surface.

2. The surgical laser system of claim 1, wherein the reference potential node is a first reference potential node and wherein the circuit further comprises a photodiode coupled between an input of the first amplifier and a second reference potential node, the photodiode being configured to receive the laser beam.

3. The surgical laser system of claim 1, wherein:
the processor is configured to start a timer when the processor receives the detection signal from the circuit; and
the processor is configured to cease propagation of the laser beam when the timer reaches a timing threshold value.

4. The surgical laser system of claim 1, wherein the processor is configured to cease propagation of the laser beam, except upon determining, based on the detection signal:
the laser beam is directed to the port;
the laser beam is propagated when the surgical laser system is directed to propagate the laser beam and not when the surgical system is not directed to propagate the laser beam; and
the laser beam is propagated within a threshold duration of time.

5. The surgical laser system of claim 1, wherein the first threshold voltage and the second threshold voltage are fixed.

6. The surgical laser system of claim 5, wherein the first threshold voltage is coupled to the negative side input of the first comparator.

7. The surgical laser system of claim 5, wherein the second threshold voltage is coupled to the negative side input of the second comparator.

8. The surgical laser system of claim 5, wherein the first threshold voltage is less than a saturation voltage of the second amplifier.

9. The surgical laser system of claim 1, wherein the input of the first comparator coupled to the output of the first amplifier is a plus side input of the first comparator.

10. The surgical laser system of claim 1, wherein the input of the second comparator coupled to the output of the second amplifier is a plus side input of the second comparator.

11. The surgical laser system of claim 1, wherein the reference potential node is a first reference potential node and wherein the circuit further comprises a photodiode coupled between an input of the first amplifier and the first reference potential node, the photodiode being configured to receive the laser beam.

12. The surgical laser system of claim 1, wherein the first comparator is configured to output a logic high voltage signal to the logic gate and the switch when the output received from the first amplifier exceeds the first threshold voltage.

13. The surgical laser system of claim 12,
wherein the switch is configured to close when the switch receives the high voltage signal from the first comparator; and
wherein the closed switch shorts the input of the second amplifier to the reference potential node.

14. The surgical laser system of claim 1, wherein the logic gate is an OR gate.

15. The surgical laser system of claim 1, wherein the output of the first comparator is directly connected to the first input of the logic gate.

16. The surgical laser system of claim 1, wherein the output of the second comparator is directly connected to the second input of the logic gate.

* * * * *